US008680986B2

(12) United States Patent
Costantino

(10) Patent No.: US 8,680,986 B2
(45) Date of Patent: Mar. 25, 2014

(54) SYSTEM AND METHOD FOR FACIAL NERVE MONITORING DURING FACIAL SURGERY

(76) Inventor: Peter Costantino, New York, NY (US)

(*) Notice: Subject to any disclaimer, the term of this patent is extended or adjusted under 35 U.S.C. 154(b) by 0 days.

(21) Appl. No.: 13/296,138

(22) Filed: Nov. 14, 2011

(65) Prior Publication Data

US 2012/0143023 A1     Jun. 7, 2012

Related U.S. Application Data

(63) Continuation-in-part of application No. 11/854,967, filed on Sep. 13, 2007, now Pat. No. 8,063,770.

(60) Provisional application No. 60/963,040, filed on Aug. 1, 2007.

(51) Int. Cl.
*G08B 1/08* (2006.01)

(52) U.S. Cl.
USPC .............. 340/539.12; 340/573.1; 600/300; 600/301; 607/62; 604/66

(58) Field of Classification Search
None
See application file for complete search history.

(56) References Cited

U.S. PATENT DOCUMENTS

| | | | | |
|---|---|---|---|---|
| 6,081,741 | A * | 6/2000 | Hollis | 600/424 |
| 7,022,072 | B2 * | 4/2006 | Fox et al. | 600/365 |
| 7,272,433 | B2 * | 9/2007 | Riff et al. | 600/510 |
| 7,382,247 | B2 * | 6/2008 | Welch et al. | 340/539.12 |
| 7,666,151 | B2 * | 2/2010 | Sullivan et al. | 600/587 |
| 7,846,094 | B2 * | 12/2010 | Miller | 600/301 |
| 2001/0031916 | A1 * | 10/2001 | Bennett et al. | 600/383 |
| 2003/0004554 | A1 * | 1/2003 | Riff et al. | 607/62 |
| 2005/0027192 | A1 * | 2/2005 | Govari et al. | 600/424 |
| 2008/0228238 | A1 * | 9/2008 | Libbus | 607/44 |
| 2008/0275349 | A1 * | 11/2008 | Halperin et al. | 600/484 |
| 2009/0054946 | A1 * | 2/2009 | Sommer et al. | 607/28 |
| 2009/0088608 | A1 * | 4/2009 | Mumford et al. | 600/300 |
| 2009/0157141 | A1 * | 6/2009 | Chiao et al. | 607/46 |
| 2009/0231125 | A1 * | 9/2009 | Baldus et al. | 340/539.12 |
| 2009/0264967 | A1 * | 10/2009 | Giftakis et al. | 607/62 |
| 2010/0036384 | A1 * | 2/2010 | Gorek et al. | 606/104 |
| 2010/0056959 | A1 * | 3/2010 | Mallinger et al. | 600/587 |

* cited by examiner

*Primary Examiner* — Julie Lieu
(74) *Attorney, Agent, or Firm* — Handal & Morofsky LLC

(57) ABSTRACT

An apparatus for monitoring the activity of a surgeon. At least one wireless sensing unit is provided for monitoring potential damage to a nerve and is located at a first location of a body being operated on by a surgeon. The wireless sensing unit senses a change in the body at the first location resulting from potential damage to the nerve occurring at a second location of the body remote from the first location. The wireless sensing unit produces a wireless sensed change output signal indicative of the change in the body which is received by a receiver and generates a corresponding received output signal. An analyzer unit receives and analyzes the received output signal to determine the change in the body. An indicator responsive to the output of said analyzer unit indicates the change in the body to indicate the potential damage to the nerve the surgeon.

24 Claims, 10 Drawing Sheets

SYSTEM AND METHOD FOR FACIAL NERVE MONITORING DURING FACIAL SURGERY

RELATED APPLICATION

This application is a non-provisional application based on and claiming the priority of U.S. patent application Ser. No. 11/854,967 filed Sep. 13, 2007 and directed to a System and Method for Facial Nerve Monitoring, which, in turn, claims the priority of provisional U.S. patent application Ser. No. 60/963,040.

FIELD OF THE INVENTION

The invention relates to the monitoring of nerve responses during surgery, and, in particular, the monitoring of facial nerves during surgery with the object of preventing permanent nerve damage.

BACKGROUND

In recent years, cosmetic surgery, and, in particular, cosmetic facial surgery is seeing dramatically increased use. This increase in the number of procedures performed each year is largely due to the fact that in the addition to the more elaborate and traditional face lift, other procedures, such as various versions of the S-lift are seeing widespread and increased performance. These procedures can be performed in one or two hours and require dramatically decreased recovery times. Moreover, such surgeries are often performed at relatively low-tech and small facilities, such as a doctor's office. Often such facilities specialize in that procedure only.

SUMMARY OF THE INVENTION

One potential complication in facial surgery is the possibility of doing damage to the facial nerves, which can result in paralysis of a portion of the face.

While equipment is available for monitoring the firing of a nerve, which can be detected (for example, by the twitching of a muscle) prior to the infliction of serious permanent injury, such systems are not used in facial surgery because the wires connecting the nerve firing transducers interfere with the performance of the surgery. Accordingly, substantial numbers of individuals undergo facial surgery today and sometimes leave the operating table with permanent nerve injury.

In accordance with the invention, apparatus is provided for monitoring the activity of a surgeon. The apparatus comprises a plurality of wireless sensing units for producing an output indicative of nerve stimulation. A receiver takes the output of the sensing units and produces at its output a plurality of signals each corresponding to the output of one of the plurality of wireless sensing units. An analyzer unit receives the plurality of signals each corresponding to the output of one of the plurality of wireless sensing units from the receiver. An indicator responds to the output of the analyzer unit.

The wireless sensing units may mechanically sense muscle movement. Alternatively, the wireless sensing units may comprise an inertial transducer. In accordance with the invention, needle electrodes are inserted into the muscle and sense electrical activity indicative of muscle activity that is the result of nerve activity due to damage or irritation. The electrodes may also be needle electrodes with two fine wires. Surface electrodes may also be used in accordance with the present invention although they are not preferred because they monitor muscle activity in a more gross manner. In contrast, intramuscular electrodes can monitor a particular muscle unit, i.e., the muscle enervated by a single nerve and that nerve, or may even be more precise.

The wireless sensing units may be powered by a battery or by induced electricity from an external electromagnetic field. The receiver is coupled to an antenna contained within a headrest cushion supporting the head of a patient being operated on. The wireless sensing units may be imprinted with an alphanumeric or other visual indicator which appears on a display unit associated with the receiver. The receiver may be coupled to a personal computer and the visual indicator may be the display of the personal computer.

The display of the personal computer may be a touch-screen, and control functions associated with the apparatus are implemented as touchably actuated icons on the touch screen. These functions may be varied and labeled in various ways by the computer. Moreover, the surgeon may select desired modes of display or labeling. In accordance with the invention, the display includes a plurality of individual displays, each of the individual displays being associated with one of the plurality of wireless sensing units. The individual displays many include an alphanumeric or other visual indicator which appears on a corresponding wireless sensing units. The individual displays may provide a meter-like indication of the amplitude of the signal produced by its respective wireless sensing units. The individual displays may change color in response to the amplitude of the signal produced by its respective wireless sensing unit.

The display may comprise a plurality of screen indicators which are positioned with respect to each other in a manner which mimics the position of the wireless position transducers. The position of the wireless sensors may be detected by the receiver and the indicator may be the screen of a personal computer, in which the position of the indicators are arranged to mimic the position of their respective wireless position transducers.

Each of the wireless sensing units may be irreversibly programmed with an indication of a particular body portion or part or the like.

In accordance with the invention, the output of the receiver may be stored for later retrieval in association with an authenticating timestamp signal.

Alternatively, the wireless sensing units may output an analog or digital signal.

The indicator may be responsive to the analyzer to generate an alarm if a predetermined threshold is exceeded. The predetermined threshold may be a threshold in change in the output of a particular wireless sensing unit over a particular period of time. The predetermined threshold may be a threshold in change in the value of a particular wireless sensing unit.

The wireless position transducers may be associated with alphanumeric or other visual indicators which correspond to corresponding indicators on the screen indicators. The appearance of the indicator may include an alphanumeric or other indication of the position of the area where damage may be occurring.

The appearance or sound of the indicator may vary in a manner which signals the seriousness of the detected condition.

Optionally, the indicator outputs a normalized signal.

Optionally, the plurality of wireless sensing units are sequentially read.

It accordance with the invention, a wireless sensing unit is a neurophysiologic monitoring/myophysiologic monitoring tack-shaped transducer/transmitter that, for example, senses muscle movement and then transmits that data to a receiver either during an operation, or in other diagnostic settings. It may be powered wirelessly via an electromagnetic field.

Alternatively, a small wafer-like battery in the transducer/transmitter housing may also be used to power the unit. In most applications, such battery power would be appropriate as it is likely that the same will function for as long as a few hours.

In accordance with the invention, a re-usable, for example, "donut-shaped" (or U-shaped) cushioned headrest supports the head of the patient during surgery. A radio antenna contained within the headrest connected to a receiver senses the output of the transducer/transmitters due to nerve activity. This output which drives a personal computer or purpose built monitoring unit receives the output from the transducer/transmitters. Likewise, electrical components housed within the headrest may be used to power the transmitter/transducers. This may be done with an electromagnetic field. The headrest (which is waterproof and can be gas sterilized) places the receiver within ten inches of the transducer/transmitter. A device placed nearby the patient or within the operating room for the receiver portion of the invention should also be contemplated.

The invention also contemplates the use of dissection instruments consisting of probes, dissecting forceps, dissecting scissors, etc. that can transmit a stimulating current, delivered to the nerve by the surgeon for purpose of locating nerves during surgery and confirming that they are either intact or damaged. The use of a milliamp stimulator "docking station" for a personal computer is contemplated in accordance with the invention. This allows the computer to control the milliamp output that is used to stimulate the nerve using the above various instruments. Additionally, a stimulator separate from the computer could be used for this purpose.

An electronic stimulator that generates a stimulating current may be integrated with the sensing computer in accordance with the invention for the purpose of stimulating the nerve to determine the ability of the transducer/transmitter to detect nerve firing and resulting movement. In accordance with the invention, it is contemplated that the surgeon or technician will control the amplitude of such stimulation. It is further contemplated that this may be done under the control of the personal computer.

In accordance with the invention is contemplated that the transducer/transmitters will be disposable or reusable.

The transducer/transmitters may contain a microchip that allows them to be selectively programmed as to the site of the body or nerve that they will be monitoring. Likewise, transducer/transmitters may also be programmed or otherwise designed so that their electronic outputs are labeled separately from each other when sensed by the receiver/computer. A hand-held programming "pen" may be used at the time of transducer/transmitter placement. The transducer/transmitter may also be irreversibly programmed at manufacture so that it can only be used for a specific area of the body (i.e., the facial nerve).

The computer software has the capability of recording the EMG data from the patient, and is capable of generating an audible tone indicating nerve firing and possible nerve injury. The inventive system also contemplates recording the data from the entire operation so that it can be retrieved, and has a mechanism by which this data is tamper proof and time-stamped so that from a legal standpoint the data can be submitted in a court of law as evidence.

The monitoring computer is provided with a screen which may show data similar to that shown by existing nerve action monitoring equipment.

In accordance with the invention, it is contemplated that a personal computer, programmed with appropriate software, may be used to monitor and process data from the transducer/transmitters.

While the intended device and method is described in the context of monitoring the facial nerve, other types of neurophysiologic, neurosensory, and motor evoked response data is contemplated as part of this invention.

In accordance with another aspect of the invention, an apparatus is provided for monitoring the activity of a surgeon. At least one wireless sensing unit is provided for monitoring potential damage to a nerve. The wireless sensing unit being located at a first location of a body being operated on by a surgeon. The wireless sensing unit senses a change in the body at the first location resulting from potential damage to the nerve occurring at a second location of the body remote from the first location. The wireless sensing unit produces a wireless sensed change output signal indicative of the change in the body. A receiver receives the wireless sensed change output signal and generates a corresponding received output signal. An analyzer unit receives and analyzes the received output signal to determine the change in the body. An indicator responsive to the output of said analyzer unit indicates the change in the body to indicate the potential damage to the nerve the surgeon.

The change in the body is caused by a nerve impulse transmitted via the nerve in response to the potential damage to the nerve occurring at the second location of the body The wireless sensing unit may include at least one of a needle electrode, a fine-wire electrode and a surface electrode. The change in the body sensed by the wireless sensing unit can be at least one of an electrical change, a chemical change and a physical change, such as a muscle twitch, a galvanic skin response change, an electrical impulse fired in a nerve, electromyographic and a chemical change, detectable from the first location of the body in response to potential damage to the nerve occurring at the second location.

The wireless sensing unit may be powered by induced electricity from an external electromagnetic field. The receiver can be coupled to an antenna contained within a headrest cushion supporting the head of the patient being operated on.

The wireless sensing units may be imprinted with an alphanumeric or other visual indicator which appears on a display unit associated with the receiver. The receiver can be coupled to a personal computer with the visual indicator being the display of said personal computer. The display of the personal computer may be a touchscreen. Control functions associated with the inventive apparatus can be implemented as programmable, and/or variable and/or touchably actuated icons on the touch screen.

The at least one wireless sensing unit can be a plurality of wireless sensing units. The analyzer unit may be a computer programmed to provide a display comprising a plurality of individual displays, each of the individual displays being associated with one of the plurality of wireless sensing units. The individual displays include an indication of an alphanumeric or other visual indicator which appears on a corresponding wireless sensing unit. The individual displays can each change color in response to the amplitude of the sensed change output signal produced by its respective wireless sensing unit. The indicator can comprise a plurality of screen indicators which are positioned with respect to each other in a manner which mimics the position of the wireless sensing units on the body of the patient being operated on. The position can be detected by the receiver with the indicator being the screen of a personal computer, in which the positions of the indicators are arranged by the computer to mimic the position of their respective wireless sensing units on the body of the patient.

The wireless sensing unit can be constructed to discriminate between movement in a direction caused by muscle nerve firing and movement having a component transverse to movement in a direction caused by muscle contraction. The wireless sensing unit can be constructed to discriminate between movements of different speed and respond to movements in a speed range of muscle nerve firing. The wireless sensing unit can be constructed to discriminate between movements of different magnitude and respond to movements in a magnitude range of muscle nerve firing. The wireless sensing unit can be constructed to discriminate between movements of different speed and respond to movements in the speed range of twitching, and discriminate between movements of different magnitude and respond to movements in a magnitude range of muscle nerve firing. The wireless sensing unit can be constructed to discriminate between movements in a direction caused by muscle nerve firing and movements having a component transverse to movement in the direction caused by muscle contraction, and discriminate between movements of different speed and respond to movements in a speed range of muscle nerve firing. The wireless sensing unit can be constructed to discriminate between movement in a direction caused by muscle nerve firing and movement having a component transverse to movement in a direction caused by muscle contraction, and discriminate between movements of different speed and respond to movements in a speed range of movement resulting from muscle nerve firing and discriminate between movements of different magnitude and respond to movements in a magnitude range of muscle nerve firing.

The wireless sensing unit can be imprinted with an alphanumeric or other visual indicator which appears on a display unit associated with the receiver. The visual indicator can an alphanumeric or other indication of a position of an area where damage to the nerve may be occurring.

The wireless sensing units can be positioned at a plurality of points on the face of a patient being operated on, the points being positioned proximate to selected facial nerves, the selected facial nerves being at risk in a particular surgery, and the points being furthered positioned, with respect to the nerves at risk, to be coupled to the nerves at risk.

In accordance with another aspect of the present invention, a method is provided for monitoring the activity of a surgeon. At least one wireless sensing unit is placed at a first location on the body of a patient being operated on by a surgeon. The wireless sensing unit is effective for sensing a change in the body at the first location resulting in response to potential damage to a nerve occurring at a second location of the body remote from the first location. The wireless sensing unit produces a wireless sensed change output signal indicative of the change in the body. The wireless sensed change output signal is received by a receive which generates a corresponding received output signal. The received output signal is analyzed to determine the change in the body. An indication is provided to the surgeon responsive to the determined change in the body for indicating to the surgeon the potential damage to the nerve. The activity of the surgeon being monitored can be, for example, performing a facial surgery such as a parotidectomy or a tympanomastoidectomy.

DESCRIPTION OF THE DRAWINGS

Several nonlimiting exemplary embodiments of the present invention are illustrated in the attached drawings, in which.

DETAILED DESCRIPTION OF THE PREFERRED EMBODIMENTS

Figure 1:
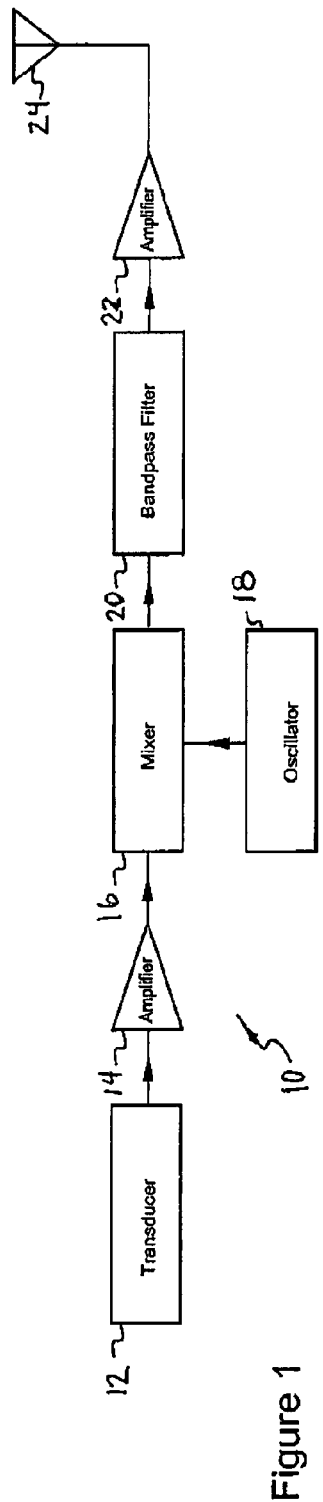
FIG. 1 is a block diagram of a nerve response transducer/transmitter constructed in accordance with the present invention.

Referring to FIG. 1, a transmitter/transducer 10 constructed in accordance with the present invention and useful in the practice of the method of the present invention is illustrated. Transmitter/transducer 10 comprises a transducer 12, of conventional design, which is adapted to detect firing of a nerve and produce an electrical output proportional to the amplitude of such firing. The same may be a movement detector such as an inertial detector, and the computer to which its output is sent, as detailed below, may have software to prevent the detection of a benign movement as a twitch signaling the onset of nerve damage. Alternatively, any other type of detector, such as electrodes similar to those used in electrocardiogram systems, may be used.

Thus, each transducer/transmitter may operate at its own unique carrier signal frequency.

The output of transducer 12 it is sent to an amplifier which amplifies a signal and sends it to a mixer 16 which acts as a modulator. Mixer 16 multiplies the output of amplifier 14 by the output of oscillator 18, forming an amplitude modulation signal with the carrier frequency equal to the frequency of oscillator 18. This amplitude modulated signal is sent to a bandpass filter 20, which removes unwanted modulation products. The filtered carrier signal with transducer information modulated onto it is then received by and amplified by amplifier 22 and output to antenna 24.

In accordance with the present invention, it is anticipated that a plurality of transducer/transmitters 10 will be placed on the face of a patient during surgery. Each of the transducer/transmitters 10 operates at a different carrier frequency, and, accordingly, transmits a separate identifiable and detectable signal indicating nerve function and, in particular, nerve firing.

These signals from a plurality of transducer/transmitters 10 may be picked up by an antenna 26 on a receiver 28. Receiver 28 comprises a tuned circuit 30 which receives the output of antenna 26 in a conventional fashion and provides its output to an RF amplifier 32. The output of RF amplifier 32 is sent to a mixer 34, which is driven by a heterodyne oscillator 36 to produce a plurality of heterodyne signals which are coupled to a plurality of signal buses 38-52, which while they each carry all heterodyne products, are each assigned to a particular heterodyne product. Heterodyne oscillator 36 operates at frequency $F_h$. Signal buses 38-52 are associated with heterodyne modulation products $F_h-F_1$, $F_h-F_2$, $F_h-F_3$, $F_h-F_4$, $F_h-F_5$, $F_h-F_6$, $F_h-F_7$, and $F_h-F_8$.

Buses 38-52 drive heterodyne product bandpass filters 54-68, respectively, which in turn drive detectors 70-84, respectively. The outputs of detectors 70-84, are provided to analog to digital converters 86-100, respectively. The outputs of these analog-to-digital converters are provided to programmable digital logic circuit 102, which may be a microprocessor, personal computer, or any other suitable device.

In accordance with the invention, the outputs of a plurality of transducer/transmitters such as those illustrated in FIG. 1 are continuously monitored by programmable digital logic 102 to provide information respecting nerve firings. Such information may be of an analog nature and may be indicated with an analog display. Alternatively, alarms may be sounded if a dangerous condition is detected. In accordance with the present invention, it is also possible to combine, for example, one or more of such alarms as visible alarms, analog readouts, audible alarms, and so forth.

One potential monitoring device is console display 104. Display 104 may be a dedicated device with suitable display members and mechanical buttons. Alternatively, display 104 may be a liquid crystal display monitor typically associated with a personal computer. In accordance with a particularly preferred embodiment of the present invention, display 104 may be a computer monitor provided with a touchscreen feature which enables the actuation of icons by the finger of a user.

In accordance with the invention, display 104 is provided with a number of indicators 106-120. In accordance with preferred embodiment illustrated in FIG. 2, display 104 is a liquid crystal touchscreen display device of conventional design. Likewise, in accordance with the preferred embodiment of the invention, programmable digital logic 102 is a personal computer.

Indicators 106-120 include numerals 122 which identify the transducer with which they are associated. Likewise, in the event that there is an indication of an alarm condition, a display 125 indicates the location of the alarm condition. The same may also be accompanied by an audible alarm.

The amplitude of signal detection is shown by conventional bar graph indicator segments 124 which may have low or normal values as illustrated by, for example, indicator 106 or high values as indicated by indicator 118. In addition, color coding may be used, for example indicator segments 124 may be green during normal operation, amber to signify a heightened alert condition, and red to indicate a dangerous condition. In accordance with the invention, it is contemplated that different audible cues will be associated with different levels of alert. For example, an amber heightened alert may be indicated by a beep, while a red dangerous condition may be indicated by a repetitive siren-like sound.

In accordance with the invention, it is contemplated that individual transmitters will be associated with a particular body part or portion of the face, for example. This may be done in a number of fashions. First the transmitter may be encoded to transmit a particular body portion identification. Alternatively, a particular use may be programmed. For example, a transducer with the number "1" printed on it may be placed by the physician and then "Select" icon 126 pushed until indicator 106 begins to blink. The surgeon or assistant would then push "Set" icon 128. The "Select" icon 126 may then be pushed repeatedly to close the sequential display of various face portion areas in display 125. Once the proper face portion appears in display 125, "Set" button 128 is depressed. Pressing "Select" button 126 then causes the next indicator 106-122 be selected.

It is also noted that, in accordance with the present invention, buttons for the surgeon or surgeon's assistant may be made to change depending on their function, with the appropriate buttons being presented at the appropriate times. Such changing may be done in systems employing a liquid crystal display device or other display device having a touch screen.

Figure 3:
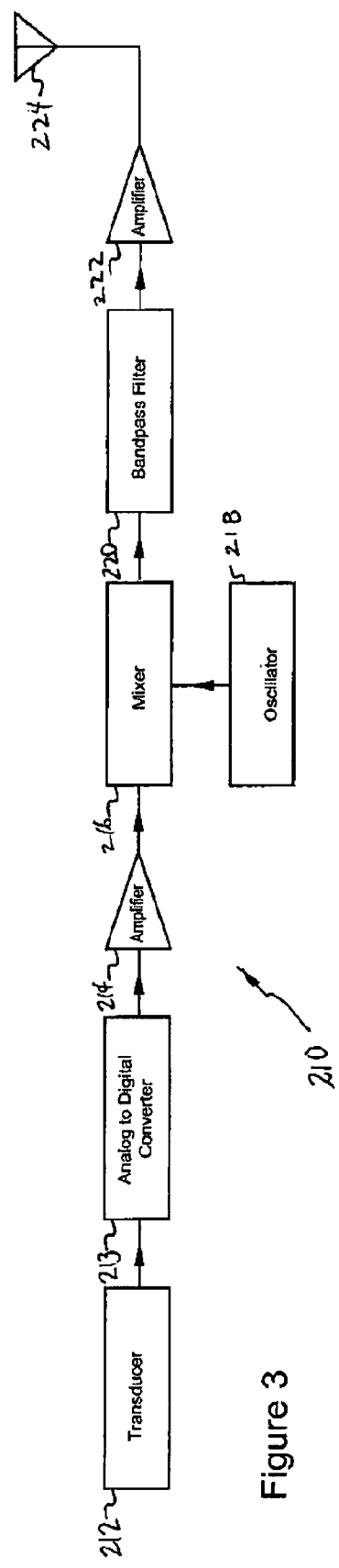
FIG. 3 is a block diagram of a transmitter similar to that of FIG. 1, except providing information in digital form.

Referring to FIG. 3, an alternative digital version of the transmitter/transducer 210 constructed in accordance with the present invention and useful in the practice of the method of the present invention is illustrated. Transmitter/transducer 210 comprises a transducer 212, of conventional design, which is adapted to detect firing of a nerve and produce an electrical output proportional to the amplitude of such firing.

The output of transducer 212 is sent to an analog to digital converter 213, which in turn, has its output sent to an amplifier 214 which amplifies the signal and sends it to a mixer 216 which acts as a modulator. Mixer 216 multiplies the output of amplifier 214 by the output of oscillator 218, forming an amplitude modulation signal with the carrier frequency equal to the frequency of oscillator 218. This amplitude modulated signal is sent to a bandpass filter 220, which removes unwanted modulation products. The filtered carrier signal with transducer information modulated onto it is then received by and amplified by amplifier 222 and output to antenna 224. Frequency modulation may also be used.

The digital transducer/transmitter illustrated in FIG. 3 has the advantage of having a numerical output guy you at the receiver which is independent of the quality of the channel coupling the transmitter to the receiver. However, the receiver is of somewhat different design, as illustrated in FIG. 4 where similar or analogous components have been numbered with numbers 200 higher than those of the corresponding components in the embodiment of FIG. 2.

Figure 4:
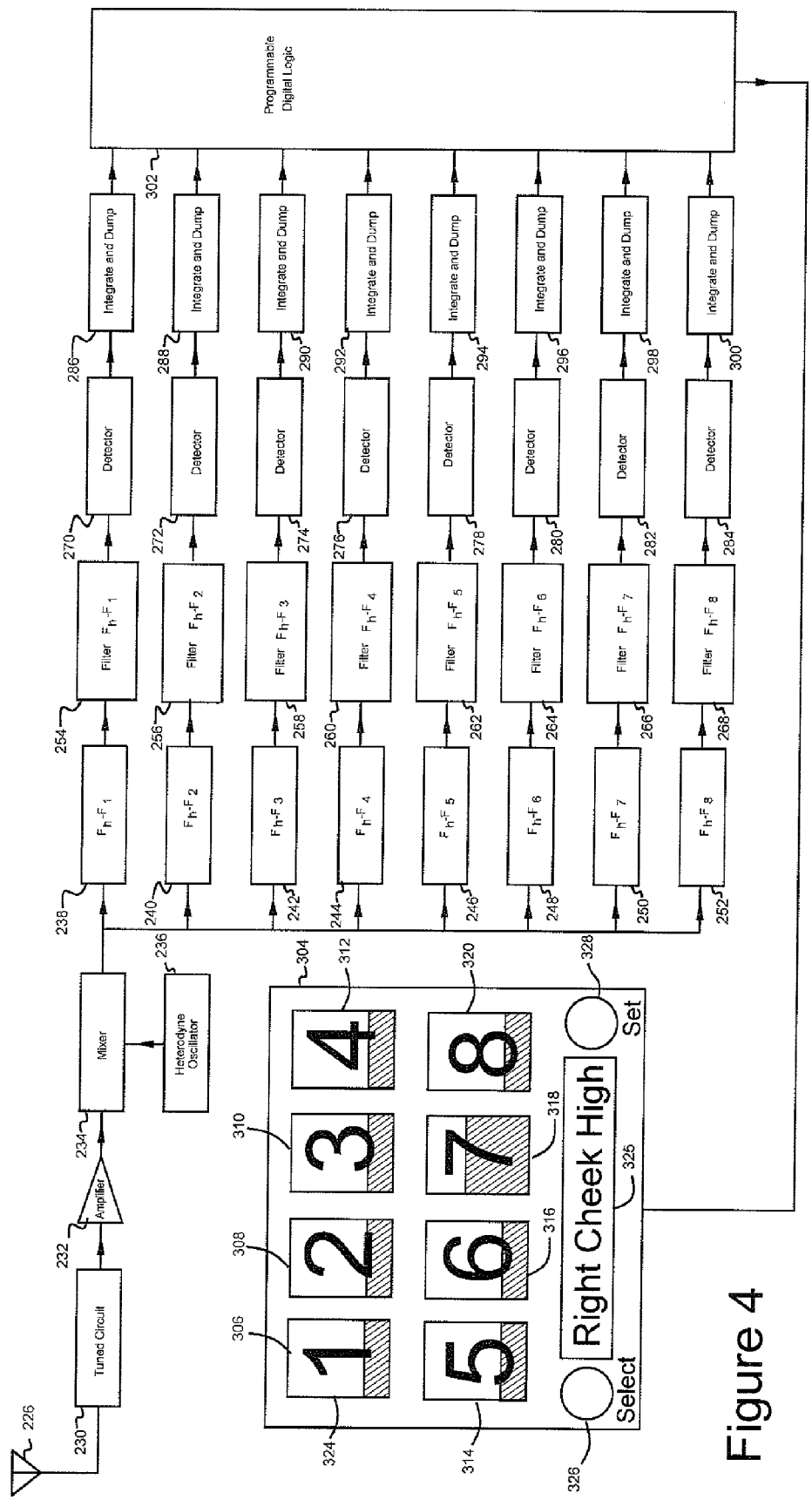
FIG. 4 is a block diagram of an alternative embodiment of the present invention useful in conjunction with the transmitter/transducer illustrated in FIG. 3.

The operation of receiver 228 illustrated in FIG. 4 is substantially identical to that of the receiver illustrated in FIG. 1, except that because the output of detectors 270-284 is already in digital form, there is no need to convert to a digital number. However, standard integrate and dump circuits 286-300 are provided to improve noise immunity.

Figure 5B:
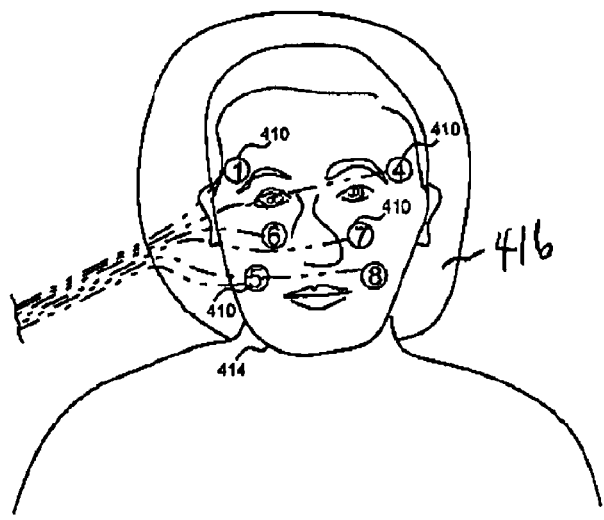
FIG. 5b is a view similar to FIG. 5a, but including wires.
Figure 5A:
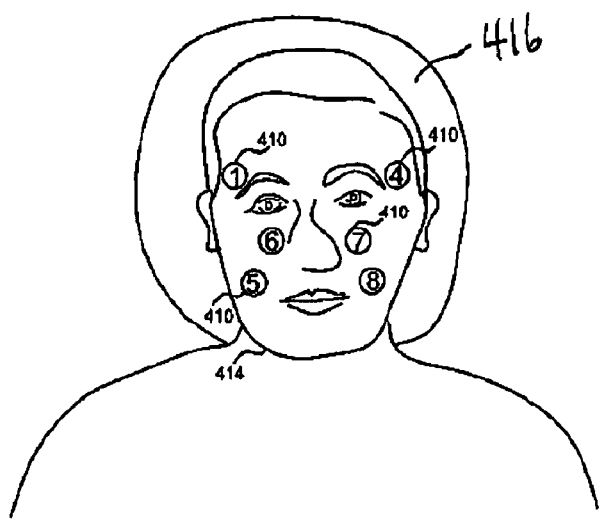
FIG. 5a shows a placement of the inventive transmitter/transducers on a facial surgery patient.

As illustrated in FIG. 5a, transducer/transmitters 410 may be placed at various portions on the face while taking up minimal space and not interfering with the performance of an operation. This would be in contrast to an arrangement in which wires 411 extending between transducers and a monitoring instrument would tend to block the area where the surgeon is working, as illustrated in phantom lines in FIG. 5b.

It accordance with the preferred embodiment, it is contemplated that transducer/transmitter units for 10 will be provided with, for example, suitable means of attachment comprising a layer of adhesive for a keen on their reverse sides, allowing them to be adhered to the skin on the face of the patient.

Figure 2:
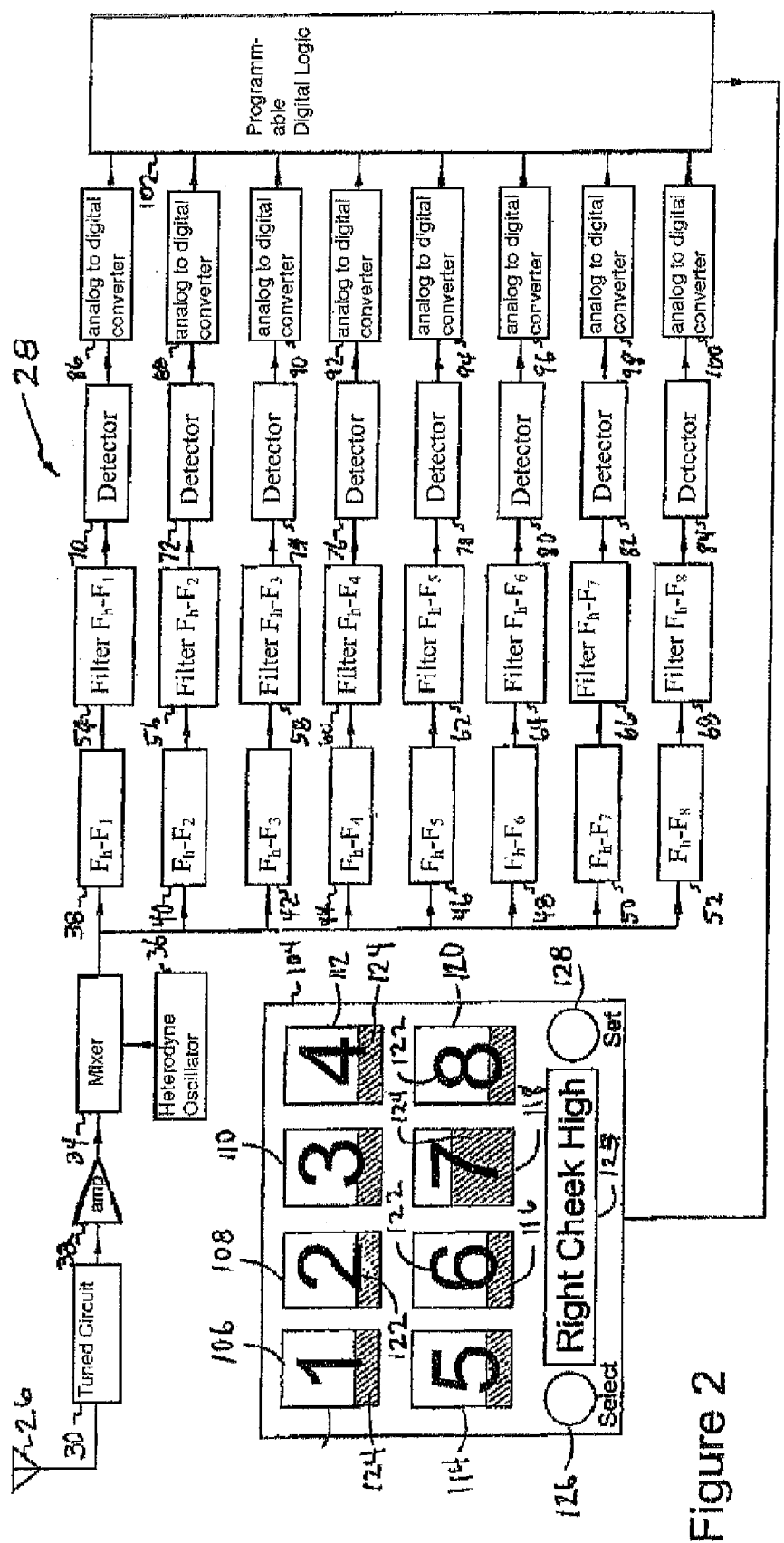
FIG. 2 is a block diagram of instrumentation for monitoring the output of the transmitter/transducer of FIG. 1.
Figure 6:
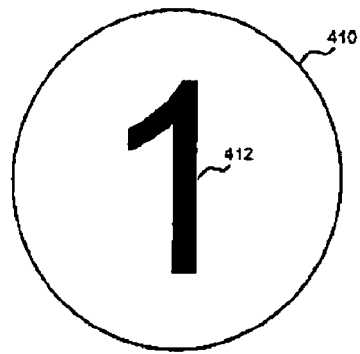
FIG. 6 is a top plan view of a transmitter/transducer constructed in accordance with the present invention and incorporating the circuitry of, for example, FIG. 1 or FIG. 2.
Figure 7:
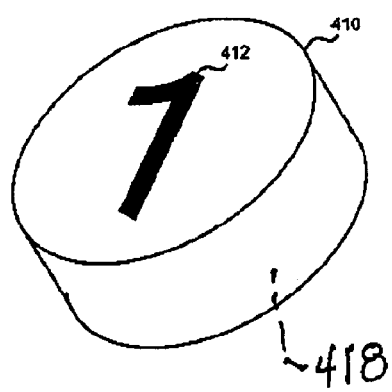
FIG. 7 is a perspective view of the transmitter/transducer of FIG. 6.

As alluded to above and as illustrated in FIGS. 6 and 7, in accordance with the present invention, individual transducer/transmitters 410 are provided with an alphanumeric indicator 412 corresponding to the alphanumerical indicators 122 in FIG. 2.

Transmitter/transducers 410 may be placed at various positions on the face 414 of a patient. Moreover, in accordance with the invention, the position of the transducers may be mimicked in the selection of receiver positions on the face of display 104. See, for example, the spatial relationship of the transducer numbers in FIG. 5 to the positions of the transducers in FIG. 2 or FIG. 4.

Antennas 26 and the radio receiver electronics may be housed in donut-shaped cushioned headset 416.

Figure 8:
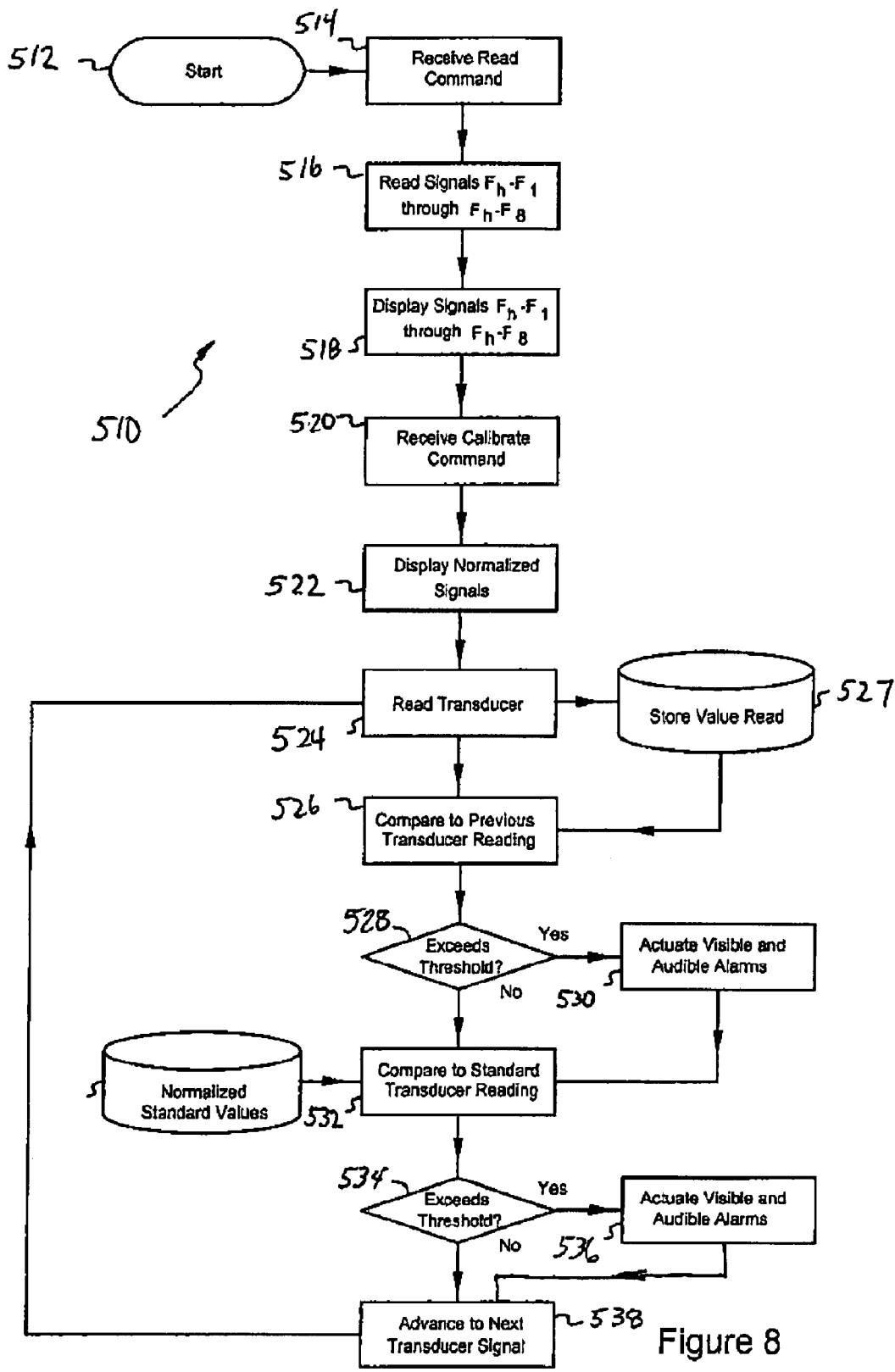
FIG. 8 is a flowchart illustrating the operation of the method of the present invention.

The inventive method of operation of the inventive systems is illustrated in FIG. 8. Method 510 begins with actuation of the system at step 512. Upon actuation, the system is ready to receive a read command at step 514. Upon the receipt of the read command, the system proceeds to read the signals output by the various transducer/transmitters placed by the surgeon on, for example, the face of the patient. The signals are read at step 516 and displayed at step 518.

At this point, the surgeon can look at the actual values being read by the transducers and determine whether the outputs are indicative of a good connection to the nerve. If a bad connection or faulty transducer/transmitter is detected, the transducer/transmitter may be reset, or replaced, as appropriate.

If desired, the surgeon has the option of normalizing the outputs of the transducers. For example such normalization may take the form of reducing the output of all transducers to zero or an appropriate low value. The surgeon may input a calibration command at step 520, causing the system to display the normalized signals on, for example, display 104 at step 522.

In accordance with the invention, the system is continuously and sequentially monitoring the outputs of all transducers/transmitters. Alternatively, such monitoring may be done simultaneously because of the frequency multiplexed nature of information transmission from individual nerves being monitored and receiver 28.

In accordance with the serial monitoring of transducer/transmitter outputs, a single transducer is read at step 524. The value of the output signal is sent to storage at step 527. The most recent value is then compared to the previous reading for that transducer at step 526 to determine potentially serious conditions. Such comparison is done by retrieving the previous value from memory. If the change in value exceeds a certain threshold, at step 528 the system proceeds to step 530 where, as appropriate, the desired visible and/or audible alarms are actuated. It accordance with the present invention, audible alarms or preferred as the surgeon need not look at the display.

The system then proceeds to step 532 where the detected value produced by the transducer is compared to a standard second threshold value believed to be indicative of a dangerous condition. Likewise, if the value detected at step 526 is not found to exceed a threshold at step 528, the system also proceeds to step 532. If the difference between the second standard value and the actual value exceeds the set threshold, at step 534 the system proceeds to step 536 to actuate, as desired, visible and/or audible alarms. After the actuation of the alarms at step 536 the system advances to the next transducer signal at step 538, as also occurs in the event that a determination is made that a threshold is not exceeded at step 534. The system then returns to step 524 to read the next transducer and determine whether a dangerous condition exist and or whether certain alarms are to be actuated.

One application of the invention involves monitoring the facial nerve, specifically electromyographic activity indicative of damage to the facial nerve, during a parotidectomy. A parotidectomy is a procedure undertaken to resect all or portions of the parotid gland.

Figure 9:
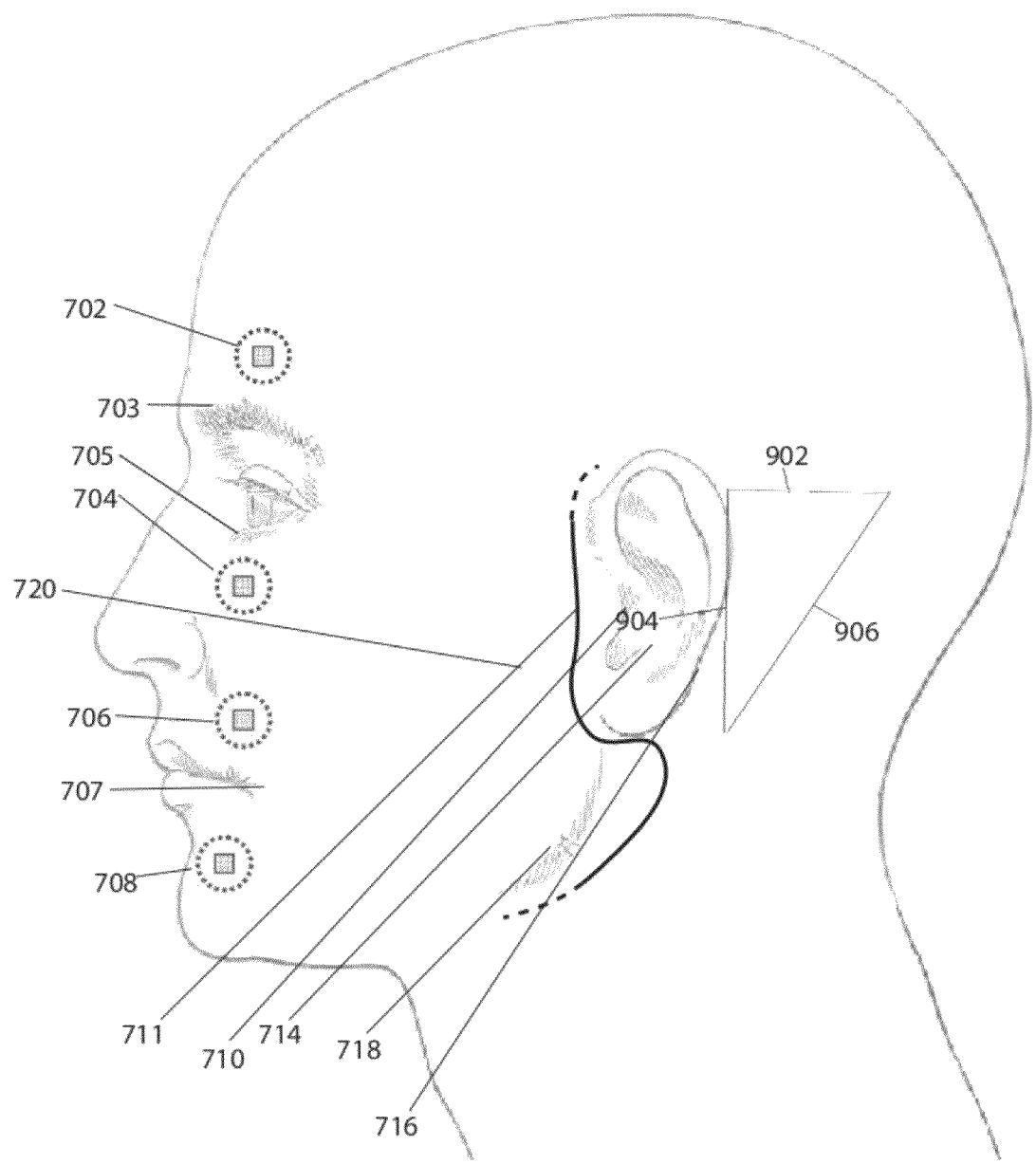
FIG. 9 is a view of transmitter/transducer placement during a surgical procedure.

FIG. 9 is a view of the transmitter/transducer placement and a surgical procedure. A plurality of transmitter/transducers 702, 704, 706, 708 are attached to the face prior to surgery. In accordance with the invention, a number of different types of transducers may be used. For example, the transducers may be of the type which include an accelerometer which detects motion of a muscle and generates an electrical signal indicative of motion. Alternatively, the transducer may also generate a signal which is indicative of the magnitude of motion. The transmitter/transducers can be 702, 704, 706, 708 wireless sensor units that may discriminate between movement in the direction caused by muscle nerve firing and movement having a component transverse to movement in the direction caused by muscle contraction, discriminate between movements of different speed and respond to movements in the speed range of movement resulting from muscle nerve firing, and discriminate between movements of different magnitude and respond to movements in the magnitude range of muscle nerve firing. The wireless sensing units or transmitters/transducers 702, 704, 706, 708 may discriminate between movements of different speed and respond to movements in the speed range of twitching and discriminate between movements of different magnitude and respond to movements in the magnitude range of muscle nerve firing.

Such indication of magnitude may be used by an algorithm which ignores, for example, relatively low magnitude motion or ignores slower motion, which may be indicated, for example, by a low-frequency content in the signal produced. More sophisticated treatment of the motion magnitude signal may also be employed. For example, certain motion may be indicative of an instrument or person touching the transducer. In addition, the direction of motion may also be monitored. This information may also be used to discriminate whether a nerve has fired or not. For example, it is known that motion in a particular direction may be indicative of a nerve being fired whereas motion in another direction may be indicative of something other than a nerve firing, and accordingly motion in such other direction would be ignored by the algorithm. Thus, a suitable algorithm may reject signals after evaluating the information they contain respecting speed, direction and displacement.

Still yet another possibility is for the transducer to detect motion by detecting electrical currents created in the muscle by the body on account of the proximity of a scalpel to the nerve. Such electrical signals may be detected, for example, by using surface electrodes, or by inserting wires (or needles) into the muscles to be monitored. In connection with this, it is noted that insertion of, for example, a needle into the muscle is preferred over using a skin surface electrode, in so far as it is less subject to interference from other electrical currents generated by the body. Accordingly, because the electrical activity which can be detected on the surface is of a relatively diffuse nature, and the electrical activity detected by a needle inserted in a muscle will be a carrier of substantially only electrical signals associated with that muscle, needle electrodes inserted in the muscle are a much more reliable indicator of actual muscle activity. Accordingly, such needle electrodes are preferred to surface electrodes in contact with the skin.

Thus, it may be useful for such transmitter/transducers 702, 704, 706, 708, to contain needle electrodes or fine-wire electrodes, which are inserted intramuscularly and may be used to detect the electrical activity of the muscle. As an example of placement, transmitter 702 is placed above the eye about 1 cm above the supraorbital rim 703 and enters the orbicularis oculi muscle. A secondary orbital transmitter 704 may be placed approximately 1 cm below the infraorbital rim 705 so that it enters the lower portion of the orbicularis oculi muscle. A superior perioral transmitter 706 can be placed approximately 1 cm above the oral commissure 707. A final transmitter 708 can be placed 1 cm below the oral commissure 707. At this point, the individual transmitters 702, 704, 706, 708 will transmit data about nerve firing to the receiver. The receiver is, in turn, connected to the display apparatus so that the surgeon may monitor nerve firing.

Figure 10A:
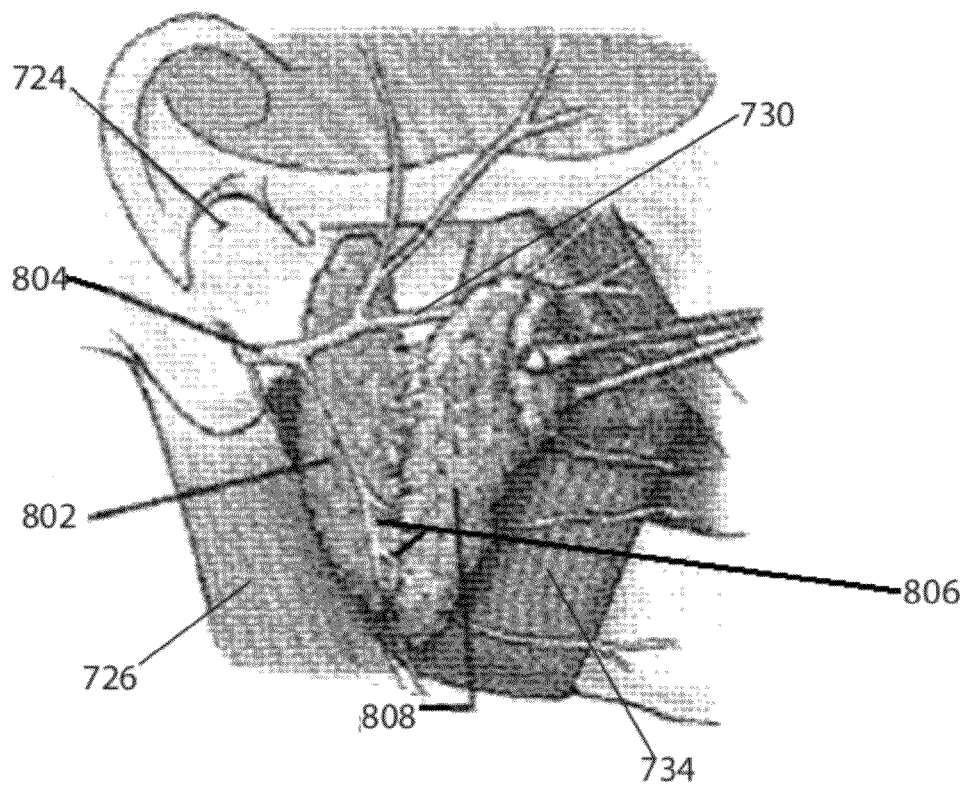
FIG. 10(a) is a view of the area surrounding a parotid gland.
Figure 10B:
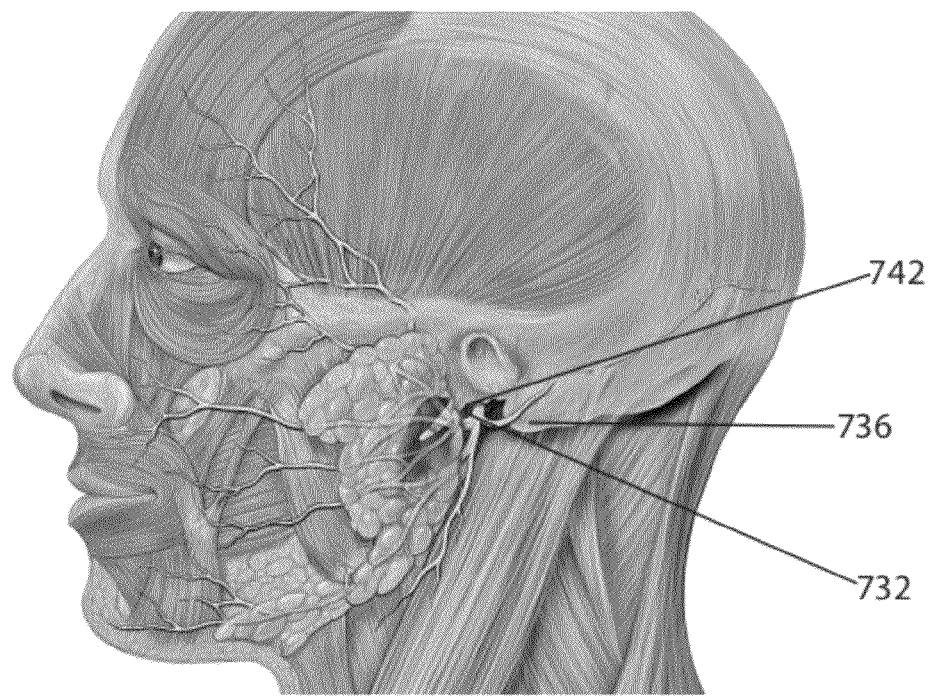
FIG. 10(b) is another view showing the area surrounding the parotid gland.

FIG. 10(a) is a view of the area surrounding a parotid gland. Referring to FIGS. 9, 10(a) and 10(b), in cases where portions of the parotid gland 802, 808 must be removed, as in a complete parotidectomy, the deep gland must be dissected out between the branches 806 of the facial nerve 804. In accordance with the present invention, a surgeon is able to monitor potential damage to a nerve, such as the facial nerve 804 and its branches 806 so as to minimize any damage in this more difficult procedure.

Referring to FIG. 9, to perform the parotidectomy, an incision 711 is started in the region of the face anterior and superior to the region of the tragus 710. The incision 711 is carried inferiorly along a skin crease down to the earlobe 714, extended around the earlobe to the postauricular area 716, and then in a curvilinear fashion brought around to a natural skin crease in the submandibular area 718. The skin is elevated in the superficial fascial layer anteriorly to expose the parotid gland 802, 808 (FIG. 10) and overlying fascia in the area of the mass to be resected. Referring again to FIG. 9, the parotid gland 802, 808 is separated from the cartilaginous external auditory canal 724 and the anterior border of the sternocleidomastoid muscle 726. The greater auricular nerve 728 is invariably identified crossing the sternomastoid muscle 726. During the surgery the transmitters 702, 704, 706, 708 will transmit data about nerve firing to the display apparatus so that the surgeon may monitor, for example, whether the postauricular branches of the auricular nerve 730 have been or are subject to damaged.

Referring again to FIG. 10(b), the stylomastoid foramen 732 is located medial to the insertion of the digastric muscle 734 on the mastoid tip 736 and the digastric muscle 734 should next be identified. Because facial paralysis can result due to damage to the facial nerve 804, great care should be employed in identifying the main trunk of the facial nerve 804. At this point the display apparatus will allow the surgeon to monitor the integrity of the facial nerve 804. The nerve 804 is encountered just inferior to the process of the external auditory canal 740 between the mastoid tip 736 and the bony external auditory meatus 742.

Referring to FIG. 10(a), when the facial nerve 804 has been identified, dissection is carried out along each of the various branches 806 dividing the gland 802, 808 in such a way as to allow the lateral lobe to be removed. The facial nerve 804 should be continuously visualized and glandular tissue should be cut along the plane of the nerve. The invention will allow the surgeon to determine whether damage is being done to the nerve during the dissection. Referring to FIG. 9, when the dissection has been carried anterior to the neoplasm 722, the tumor is removed. In malignancies or benign lesions extending deep to the nerve, the surgeon must decide if any of the branches must be sacrificed in order to completely remove gross and or microscopic disease.

Referring to FIG. 10(a), in cases where portions of the parotid gland 802,808 beneath the facial nerve 804 must be removed, as in a complete parotidectomy, the deep lobe of the parotid gland 802 must be dissected out between the branches 806 of the facial nerve 804. In accordance with the present invention, a surgeon can monitor potential damage to the facial nerve 804 and its branches 806 so as to minimize any damage in this more difficult procedure.

Figure 11:
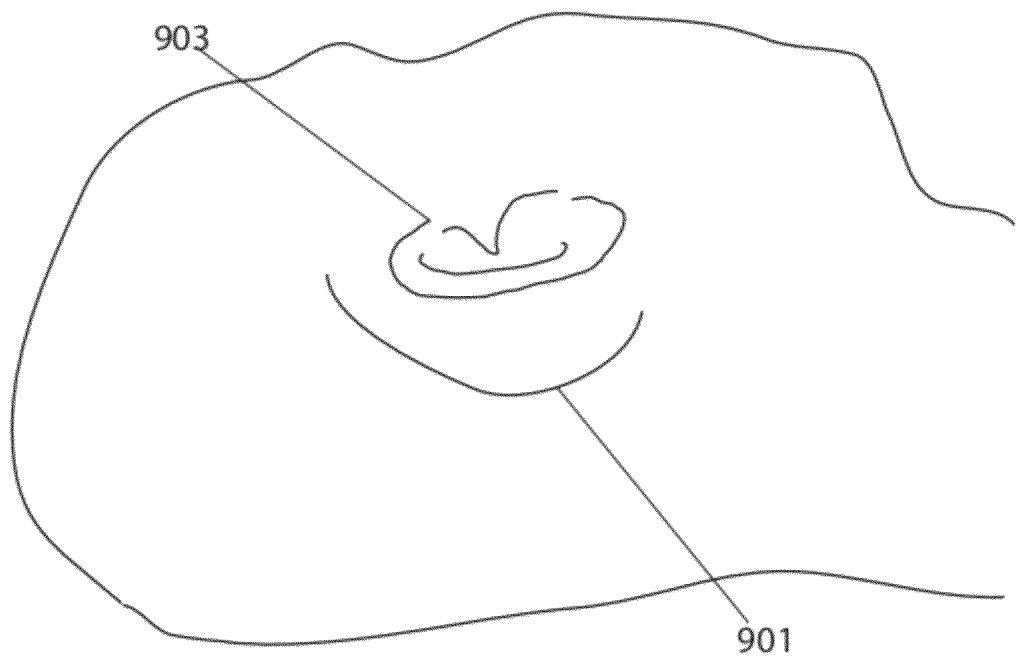
FIG. 11 is a view of a the head of a patient undergoing a tymanomastoidectomy procedure.

Another possible application of the invention involves monitoring the facial nerve 804, specifically electromyographic activity indicative of damage to the facial nerve, during a tympanomastoidectomy. A tymanomastoidectomy is an excision of the mastoid air cells and the tympanic membrane. FIG. 11 is a view of a the head of a patient undergoing a tymanomastoidectomy procedure To perform a tympanomastoidectomy, an incision 901 is made behind the ear 903 of the patient.

Referring to FIG. 9, as in the parotidectomy, the plurality of transmitter/transducers 702,704,706,708 are attached to the face prior to surgery. In accordance with the invention, it may be useful for such transmitter/transducers 702,704,706,708 to contain needle electrodes or fine-wire electrodes, which are inserted intramuscularly and may be used to detect the electrical activity of the muscle. As with the example of the parotidectomy, as an example of placement, transmitter 702 is placed above the eye about 1 cm above the supraorbital rim 703 and enters the orbicularis oculi muscle. A secondary orbital transmitter 704 may be placed approximately 1 cm below the infraorbital rim 705 so that it enters the lower portion of the orbicularis oculi muscle. A superior perioral transmitter 796 can be placed approximately 1 cm above the oral commissure 707. A final transmitter 708 can be placed 1 cm below the oral commissure 709. At this point, the individual transmitters 702, 704, 706, 708 will transmit data about nerve firing to the receiver. The receiver is, in turn, connected to the display apparatus so that the surgeon may monitor nerve firing.

Referring again to FIG. 9, the location of entry into the head of the patient for performing the tymanomastoidectomy is indicated. A large cutting burr is used to begin drilling. Cuts are made parallel to the linea temporalis 902 and then posterior to the external auditory canal to create a ninety-degree angle 904. The third side of the triangle roughly approximates the course of the sigmoid sinus 906 posteriorly.

Figure 12:
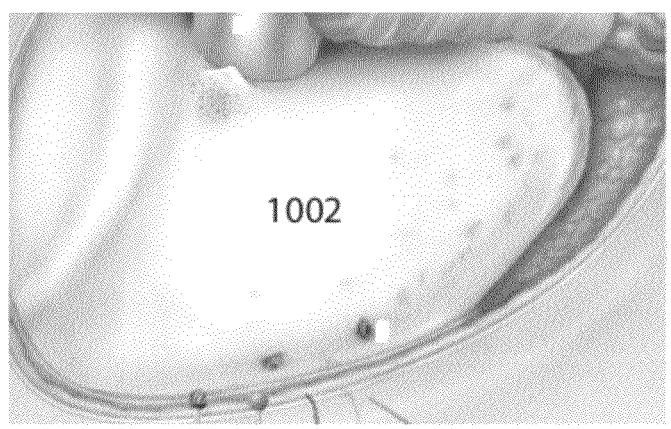
FIG. 12 is a view of a mastoid cortex.
Figure 13:
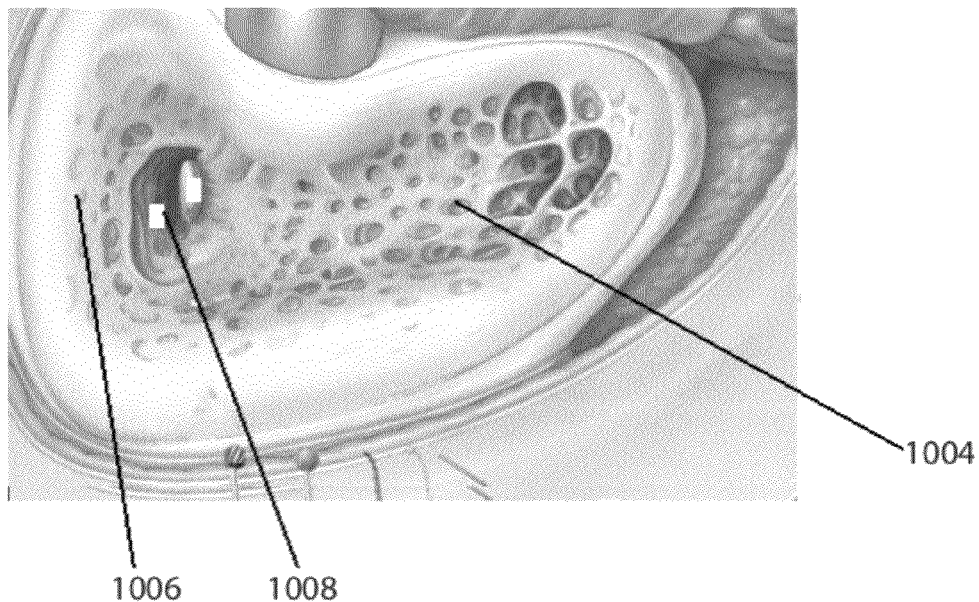
FIG. 13 is a view deep to a mastoid cortex in which air cells are exposed.
Figure 14:
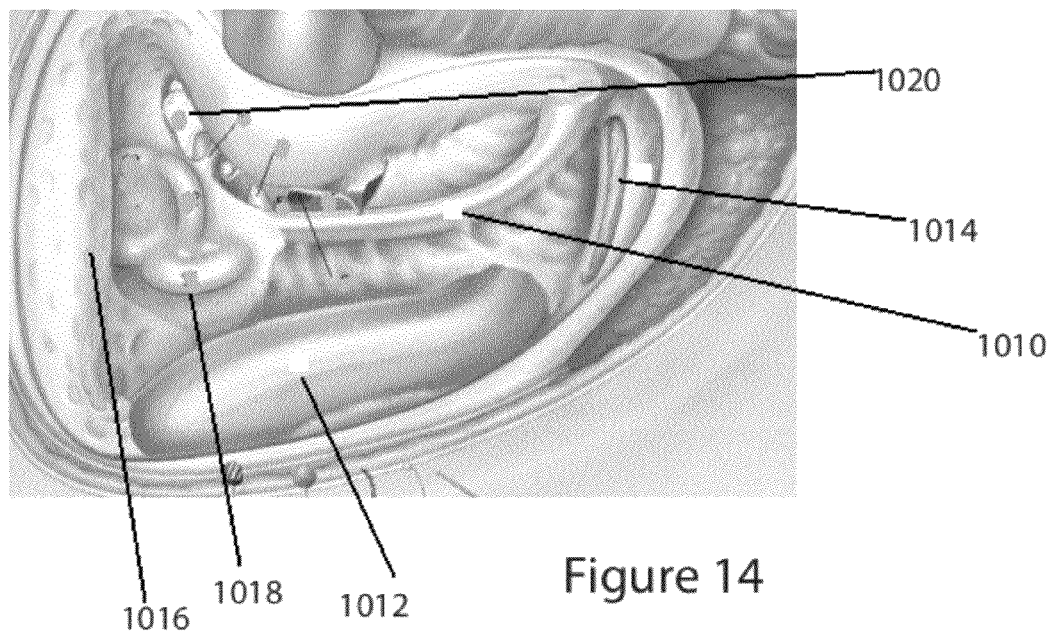
FIG. 14 is a view deep to mastoid air cells in which an antrum may be visualized.

Referring to FIG. 12, the mastoid cortex 1002 is removed. Referring to FIG. 13, the air cell system 1004 is then exposed. Drilling proceeds with identification of the tegmen mastoideum 1006 through bone. The deepest point of the dissection should always be centered over the antrum 1008. Referring to FIG. 14, this ensures that the antrum 1008 with its critical landmarks will be entered before reaching the plane of the facial nerve 1010. The sigmoid sinus 1012 will come into view posteriorly. The digastric ridge 1014 can be identified posteriorly; the cephalic edge of this ridge provides an important landmark for the course of the vertical portion of the facial nerve 1010.

Körner's septum 1016 will be present to a varying degree just lateral to the mastoid antrum 1008. Referring to FIG. 13, using the tegmen 1006 as the superior landmark and the posterior canal wall as the anterior landmark, Koerner's septum 1016 is removed and the antrum is entered. This step highlights the importance of identifying the tegmen 1006 and following it toward the antrum 1008. Failure to identify the tegmen 1006 may result in injury to the horizontal semicircular canal 1018 and facial nerve 1010 (FIG. 14). Monitoring this process with the invention's display apparatus at this point will assist the surgeon in avoiding such injury to the nerve.

Figure 15:
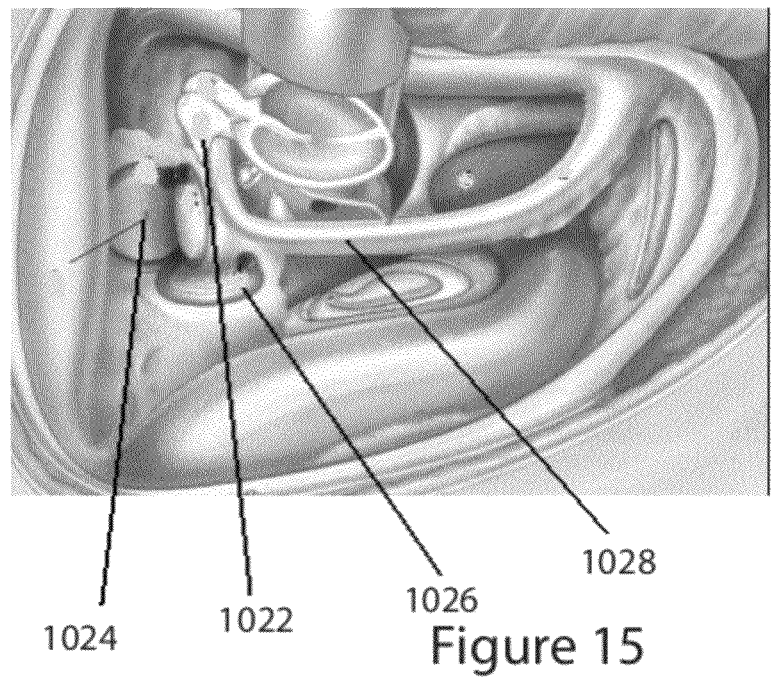
FIG. 15 is a view of the area external to an ear canal.

Once the antrum 1008 has been entered, cholesteatoma matrix or mucosal disease should be removed. The short process of the incus should be identified. Drilling continues toward the root of the zygoma until the incus is seen in the fossa includes 1020. Referring to FIG. 15, the completed intact canal wall mastoidectomy should be bounded by a thin but intact middle fossa plate 1024, the sigmoid sinus should be visible through intact bone, the posterior wall of the external ear canal should be thinned yet intact, the short process of the incus 1022 should be visible the horizontal canal 1026 should be clearly identifiable. Damage to the facial nerve 1028 is prevented through constant monitoring of the display apparatus of the invention to be sure that it is preserved throughout this process as the surgeon proceeds from landmark to landmark.

Figure 16:
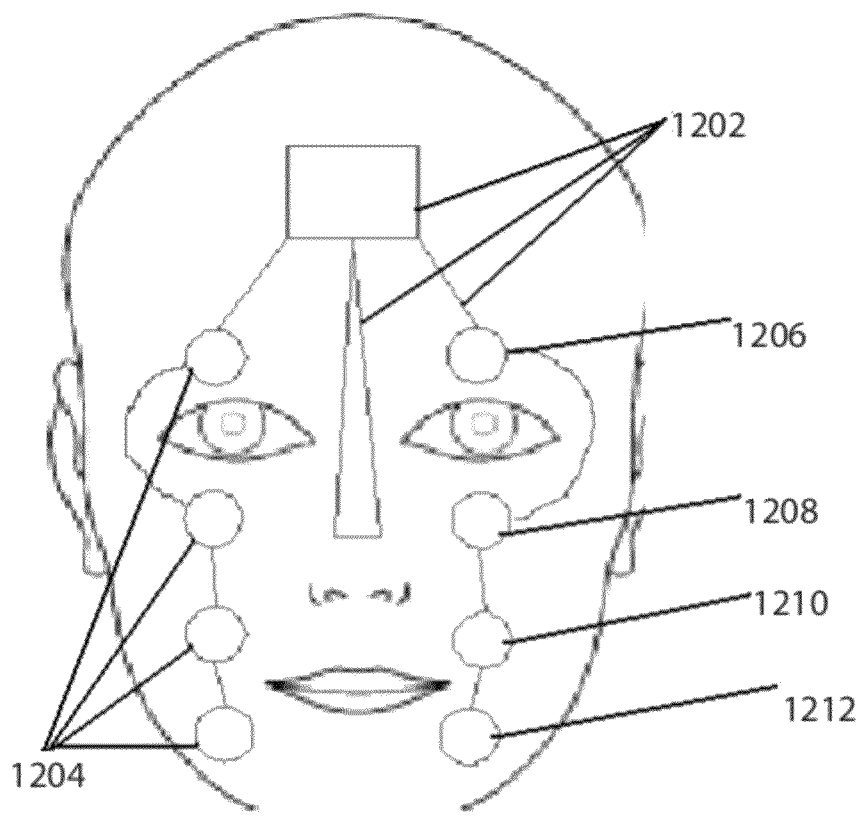
FIG. 16 illustrates a flexible printed circuit device for insuring proper placement of the transducers, showing a common transceiver associated with the transducers.

FIG. 16 illustrates a flexible printed circuit device for insuring proper placement of the transducers, showing a common transceiver associated with the transducers. In accordance with this aspect of the invention, a mask is comprised of a flexible circuit with an array of transducers 2004, 1206, 1208, 1210 and 1212. The transducers 2004, 1206, 1208, 1210 and 1212 may contain either a surface electrode or a needle electrode which can insert directly into the facial muscle fibers. The array extends to cover the face, including points adjacent the mouth, overlying the cheeks and at the level of the eyebrows on either side. The mask arrays will be interconnected to one another, such as via a flexible printed circuit, and have a single or multiple wireless transmitters 1202 to alert the receiver of an electromechanical nerve depolarization event.

With respect to the above description, it is realized that the optimum dimensional relationships for parts of the invention, including variations in size, materials, shape, form, function, and manner of operation, assembly and use, are deemed readily apparent and obvious to one skilled in the art. All equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described. Accordingly, all suitable modifications and equivalents may be resorted to, falling within the scope of the invention.

The invention claimed is:

1. Apparatus for monitoring the activity of a surgeon, comprising: (a) at least one wireless sensing unit for monitoring potential damage to a nerve, said wireless sensing unit being located at a first location of a body being operated on by a surgeon and being effective for sensing a change in the body at the first location resulting in response to potential damage to the nerve occurring at a second location of the body remote from the first location and producing a wireless sensed change output signal indicative of the change in the body; (b) a receiver capable of receiving the wireless sensed change output signal and generating a corresponding received output signal; (c) an analyzer unit for receiving and analyzing the received output signal to determine the change in the body; and (d) an indicator responsive to the output of said analyzer unit for indicating the change in the body to indicate the potential damage to the nerve to the surgeon.

2. Apparatus for monitoring the activity of a surgeon according to claim 1; wherein said wireless sensing unit includes at least one of a needle electrode, a fine-wire electrode and a surface electrode; and wherein the change in the body is caused by a nerve impulse transmitted via the nerve in response to the potential damage to the nerve occurring at the second location of the body.

3. Apparatus for monitoring the activity of a surgeon according to claim 2; wherein the change in the body comprises at least one of an electrical change, a chemical change and a physical change.

4. Apparatus for monitoring the activity of a surgeon according to claim 3; wherein the change in the body comprises at least one of a muscle twitch, a galvanic skin response change, an electrical impulse fired in a nerve, electromyographic, and a chemical change, detectable from the first location of the body in response to potential damage to the nerve occurring at the second location.

5. Apparatus for monitoring the activity of a surgeon according to claim 1; wherein said wireless sensing unit is powered by induced electricity from an external electromagnetic field.

6. Apparatus for monitoring the activity of a surgeon according to claim 1; wherein said receiver is coupled to an antenna contained within a headrest cushion supporting the head of a patient being operated on.

7. Apparatus for monitoring the activity of a surgeon according to claim 1; wherein said wireless sensing units are imprinted with an alphanumeric or other visual indicator which appears on a display unit associated with said receiver.

8. Apparatus for monitoring the activity of a surgeon according to claim 7; wherein said receiver is coupled to a personal computer and said visual indicator is the display of said personal computer, and wherein said display of said personal computer is a touchscreen, and control functions associated with said apparatus are implemented as programmable, and/or variable and/or touchably actuated icons on said touch screen.

9. Apparatus for monitoring the activity of a surgeon according to claim 1; wherein said at least one wireless sensing unit comprises a plurality of wireless sensing units; and wherein said analyzer unit is a computer programmed to provide a display comprising a plurality of individual displays, each of said individual displays being associated with one of said plurality of wireless sensing units, and wherein said individual displays include an indication of an alphanumeric or other visual indicator which appears on a corresponding wireless sensing unit.

10. Apparatus for monitoring the activity of a surgeon according to claim 9; wherein said at least one wireless sensing unit comprises a plurality of wireless sensing units; and wherein said individual displays each change color in response to said amplitude of said signal produced by its respective wireless sensing unit.

11. Apparatus for monitoring the activity of a surgeon according to claim 1; wherein said at least one wireless sensing unit comprises a plurality of wireless sensing units; and wherein said indicator comprises a plurality of screen indicators which are positioned with respect to each other in a manner which mimics a position of said wireless sensing units.

12. Apparatus for monitoring the activity of a surgeon according to claim 11; wherein the position is detected by said receiver and the indicator is the screen of a personal computer, in which the positions of the indicators are arranged by said computer to mimic the position of their respective wireless sensing units.

13. Apparatus for monitoring the activity of a surgeon according to claim 1; wherein said wireless sensing unit discriminates between movement in a direction caused by muscle nerve firing and movement having a component transverse to movement in a direction caused by muscle contraction.

14. Apparatus for monitoring the activity of a surgeon according to claim 1; wherein said wireless sensing unit discriminates between movements of different speed and responds to movements in a speed range of muscle nerve firing.

15. Apparatus for monitoring the activity of a surgeon according to claim 1; wherein said wireless sensing unit discriminates between movements of different magnitude and responds to movements in a magnitude range of muscle nerve firing.

16. Apparatus for monitoring the activity of a surgeon according to claim 1; wherein said wireless sensing unit discriminates between movements of different speed and responds to movements in the speed range of twitching and discriminate between movements of different magnitude and respond to movements in a magnitude range of muscle nerve firing.

17. Apparatus for monitoring the activity of a surgeon according to claim 1; wherein said wireless sensing unit discriminates between movements in a direction caused by muscle nerve firing and movements having a component transverse to movement in the direction caused by muscle contraction and discriminates between movements of different speed and responds to movements in a speed range of muscle nerve firing.

18. Apparatus for monitoring the activity of a surgeon according to claim 1; wherein said wireless sensing unit discriminates between movement in a direction caused by muscle nerve firing and movement having a component transverse to movement in a direction caused by muscle contraction and discriminates between movements of different speed and responds to movements in a speed range of movement resulting from muscle nerve firing and discriminates between movements of different magnitude and responds to movements in a magnitude range of muscle nerve firing.

19. Apparatus for monitoring the activity of a surgeon according to claim 1; wherein said wireless sensing unit is imprinted with an alphanumeric or other visual indicator which appears on a display unit associated with said receiver.

20. Apparatus for monitoring the activity of a surgeon according to claim 1; wherein said indicator includes an alphanumeric or other indication of a position of an area where damage to the nerve may be occurring.

21. Apparatus for monitoring the activity of a surgeon according to claim 1; wherein said at least one wireless sensing unit comprises a plurality of wireless sensing units positioned at a plurality of points on the face of a patient being operated on, the points being positioned proximate to selected facial nerves, the selected facial nerves being at risk in a particular surgery, and the points being furthered positioned, with respect to the nerves at risk, to be coupled to the nerves at risk.

22. A method for monitoring the activity of a surgeon, comprising: (a) placing at least one wireless sensing unit for monitoring potential damage to a nerve, said wireless sensing unit being placed at a first location of a body being operated on by a surgeon and being effective for sensing a change in the body at the first location resulting in response to potential damage to the nerve occurring at a second location of the body remote from the first location and producing a wireless sensed change output signal indicative of the change in the body; (b) receiving the wireless sensed change output signal and generating a corresponding received output signal; (c) receiving and analyzing the received output signal to determine the change in the nerve; and (d) providing an indication to the surgeon responsive to the determined change in the body for indicating to the surgeon the potential damage to the nerve.

23. A method for monitoring the activity of a surgeon according to claim 22; wherein said activity of the surgeon comprises performing a parotidectomy.

24. A method of monitoring the activity of a surgeon according to claim 22; wherein the activity of said surgeon comprises performing a tympanomastoidectomy.

* * * * *